(12) United States Patent
Sodemann

(10) Patent No.: US 6,423,706 B2
(45) Date of Patent: *Jul. 23, 2002

(54) ANTIMICROBIAL LOCKS COMPRISING TAURINAMIDE DERIVATIVES AND CARBOXYLIC ACIDS AND/OR SALTS THEREOF

(75) Inventor: Klaus Sodemann, Lahr (DE)

(73) Assignee: Biolink Corporation, Norwell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/741,321

(22) Filed: Dec. 20, 2000

Related U.S. Application Data

(63) Continuation-in-part of application No. 09/307,916, filed on May 10, 1999, now Pat. No. 6,166,007.
(60) Provisional application No. 60/091,491, filed on Jul. 2, 1998.

(51) Int. Cl.$^7$ ................................................ A61K 31/54
(52) U.S. Cl. .................. 514/222.5; 514/223.2
(58) Field of Search ............................ 514/222.5, 223.2

(56) References Cited

U.S. PATENT DOCUMENTS 5,210,083 A * 5/1993 Pfirrmann ................ 514/222.5
6,166,007 A * 12/2000 Sodemann ............... 514/222.5

* cited by examiner

*Primary Examiner*—Kevin E. Weddington
(74) *Attorney, Agent, or Firm*—William & Associates; Frederick C. Williams; Yan Lan

(57) ABSTRACT

The present invention relates to a method of inhibiting or preventing infection and blood coagulation in or near a medical prosthetic device after said device has been inserted in a patient comprising administering to the device a pharmaceutically effective amount of a composition comprising:

(A) at least one taurinamide derivative, and (B) at least one compound selected from the group consisting of biologically acceptable acids and biologically acceptable salts thereof, whereby there are no systemic anti-clotting and no systemic biocidal effects.

4 Claims, No Drawings

ANTIMICROBIAL LOCKS COMPRISING TAURINAMIDE DERIVATIVES AND CARBOXYLIC ACIDS AND/OR SALTS THEREOF

In addition, the benefit of U.S. application No. 09/307,916, filed May 10, 1999, to be issued Dec. 26, 2000 as U.S. Pat. No. 6,166,007, as a continuation-in-part, is also claimed.

The benefit of copending U.S. Provisional Application No. 60/091,491, filed Jul. 2, 1998 is hereby claimed.

BACKGROUND OF THE INVENTION

1. Field of the Invention

The present invention relates to a composition and method for the flushing and coating of catheters for the prevention of infection and blood coagulation.

2. Description of Related Art

Hemodialysis access systems for access to a human or animal patient's vascular system for exchange of blood between the vascular system and an external processing apparatus are well known in the art. One method comprises a catheter placed in the patient with one end extending into the central venous system. As with any invasive procedure, the prevention of infection has been a problem, particularly with a device that must remain in place over protracted periods of time. Coagulation of the blood in and around the catheter has also proven troublesome and methods are needed for its prevention, particularly with regard to inhibiting the clogging of the catheter, which can diminish or destroy its usefulness. A significant amount of research has been directed to the alleviation of these problems.

It is standard procedure to flush catheters with an anticoagulant, such as heparin. However, heparin is not an antibacterial and, in addition, if not carefully controlled, it can carry the anti-coagulation process too far, thereby presenting a risk of hemorrhage.

U.S. Pat. No. 4,096,241 discloses pharmaceutical compositions for the treatment and for prophylaxis of tooth and gum infections, and in particular parodontosis, comprising derivatives of thiadiazine as the active ingredient.

U.S. Pat. No. 4,107,305 discloses a method of combating endotoxaemia by administering an effective amount of a taurolin composition.

U.S. Pat. No. 4,337,251 discloses the use of taurolin in humans or animals to eliminate or reduce adhesions after surgery.

U.S. Pat. No. 4,587,268 discloses a composition for the treatment of wounds comprising a resorbable aqueous gel having dissolved or dispersed therein one or more water-soluble medicaments, which are preferably an antibiotic or a methylol transfer antibacterial.

U.S. Pat. No. 4,587,284 discloses the preparation of an enhanced water-absorbency hydrophilic polymer material, suitable for use in wound dressings by a process in which a water-containing organic hydrogel comprising a gelable polysaccharide and/or protein or polypeptide interspersed with a polymer of a hydrophilic acrylic or methacrylic acid derivative is permeated with a base, the pH of said hydrogel being raised to at least 9 during treatment with said base.

U.S. Pat. No. 4,604,391 discloses the administration of taurolin compounds prophylactically to humans or warm-blooded animals to combat the occurrence of osteitis or osteomyelitis, especially in patients suffering from bone injuries of traumatic origin.

U.S. Pat. No. 4,626,536 discloses the use of taurolin compounds to combat toxic proteins or peptides, e.g., venoms, fungal toxins and bacterial exotoxins, in the bloodstream of humans or warm-blooded animals.

U.S. Pat. No. 4,772,468 discloses a pharmaceutical composition for filling into bone cavities comprising an aqueous paste formed from powdered calcium phosphate and an antibacterial substance, if necessary together with one or more binders. The antibacterial substance is preferably taurolidine and the calcium phosphate is preferably β-tricalcium phosphate.

U.S. Pat. No. 4,797,282 discloses a drug depot, which can be implanted in the body, for the controlled, delayed release of cytostatics, comprising a synthetic material based on polyacrylates and/or polymethacrylates containing a cytostatic and at least one amino acid.

U.S. Pat. No. 4,853,225 discloses an implantable medicament depot useful for combating infections comprising physiologically acceptable excipients and at least one delayed release active compound that is a chemotherapeutic of the gyrase inhibitor type.

U.S. Pat. No. 4,882,149 discloses a pharmaceutical depot preparation for implantation into base tissue comprising natural bone mineral from which the naturally associated fat and bone-proteins have been removed whereby said bone is sterile and non-allergenic, said bone material having adsorbed thereon and/or absorbed therein one or more physiologically active substances. The physiologically active substance is advantageously an antibiotic or taurolidine or taurultam or a protein or polypeptide assisting bone regeneration.

U.S. Pat. No. 4,905,700 discloses an acoustic coupling medium for transmitting ultra-sound. The medium, which is of use in ultrasonic visualization of the human body, comprises a sheet of hydrogel containing over 90% water, preferably over 95% water. The hydrogel preferably comprises agar, the chains of which are interspersed with chains of polyacrylamide.

U.S. Pat. No. 4,960,415 discloses a device for inserting in wounds and wound cavities consisting of a container containing a pharmaceutically active substance, the walls of this container consisting at least partly of a membrane, preferably a semi-permeable membrane, which allows the active substance to escape into the wound area. The container is, more preferably, a dialysis tube. In order to drain off wound secretions, the container containing the pharmaceutically active substance, particularly taurolidine, is conveniently connected to a drainage tube. Preferably, a drainage tube is used in which the end that leads into the wound is split into filaments.

U.S. Pat. No. 5,077,281 discloses the use of taurolin compounds as blood coagulation-inhibiting agents and as abacterial inflammation-inhibiting agents. According to the patent, taurolin has outstanding coagulation-inhibiting action and is especially suitable for use in medical conditions requiring dialysis and for vascular prostheses. It is also disclosed that these compounds can be used together with other anti-coagulants such as coumarin or heparin.

U.S. Pat. No. 5,167,961 and 5,417,975 disclose processes for the preparation of high purity bone mineral wherein the organic matter is degraded by heating with ammonia or a primary amine, characterized in that the solubilized degradation products are extracted by washing with flowing water at a temperature below 60° C., such heating with primary amine and washing steps optionally being repeated, whereby substantially all organic matter removable by these steps is removed, the bone mineral so treated being heated in air at temperatures up to 700° C.

U.S. Pat. No. 5,210,083 discloses an aqueous solution containing a bacterially effective concentration of taurolidine and/or taurultam together with a parenterally acceptable polyol. The aqueous solution is said to be particularly suitable for parenteral administration.

U.S. Pat. No. 5,362,754 discloses pharmaceutical compositions of a mixture of minocycline and EDTA (M-EDTA) and methods of using the compositions in maintaining the patency of a catheter port. Methods for inhibiting the formation of polysaccharide-rich glycocalyx (such as the glycocalyx of staphylococcal organisms) are also provided using an M-EDTA solution. The M-EDTA solution may also be used to pretreat a medical device to prevent adherence of infectious organisms, such as *S. epidermis* and *S. aureous*. The compositions destroy and prevent the formation of polysaccharide-rich glycocalyx.

U.S. Pat. No. 5,573,771 discloses a purified particulate bone mineral product for use in medicine, the particles of said mineral being substantially free from all endogenous organic material and having at least at the surface thereof resorbable, physiologically compatible, natural or synthetic macromolecular material In particular, a bone mineral is provided that is impregnated with a gel-forming protein or polysaccharide such as gelatin to provide an increase in strength and a product comprising bone mineral in a matrix of collagen-fibers and a gel-forming protein. Such products are intended as remodeling implants or prosthetic bone replacement.

U.S. Pat. No. 5,593,665 discloses products containing tumor necrosis factor and taurolidine and/or taurultam as a combined preparation for simultaneous, separate or sequential use for treatment of patients suffering from medical conditions mediated by tumor necrosis factor.

U.S. Pat. No. 5,603,921 discloses a medicated dental floss for controlling the bacterial activity associated with gingivitis. The floss incorporates an antimicrobial agent which, as a result of the flossing action, is deposited to the interdental area of the teeth. The slow dissolution of the antimicrobial agent ensures that effective levels of medication are attained for sustained periods, thereby reducing bacterial activity.

U.S. Pat. No. 5,688,516 discloses compositions and methods of employing compositions in flushing and coating medical devices. The compositions include selected combinations of a chelating agent, anticoagulant, or antithrombotic agent, with a non-glycopeptide antimicrobial agent, such as the tetracycline antibiotics. Methods for using these compositions for coating a medical device and for inhibiting catheter infection are also disclosed. Particular combinations include minocycline or other non-glycopeptide antimicrobial agent together with EDTA, EGTA, DTPA, TTH, heparin and/or hirudin in a pharmaceutically acceptable diluent.

Myers et al., *J. Appl. Bacteriol* 48:89–96 (1980) reported that taurolin-bis(1,1-dioxo-perhydro-1,2,4 thiadiazinyl) methane—is an antimicrobial compound formed by the condensation of two molecules of taurine with three of formaldehyde. It had been previously suggested that taurolin releases formaldehyde in contact with bacteria. The authors presented evidence that indicated that taurolin is mostly hydrolyzed in aqueous solution to release one molecule of formaldehyde and two monomeric molecules, 1,1-dioxoperhydro-1,2,4-thiadiazine and its carbinolamine derivative. According to the article, a stable equilibrium was established. The authors concluded that antibacterial activity was not entirely due to adsorption of free formaldehyde, but also to reaction with a masked (or latent) formaldehyde, as the activity of taurolin was found to be greater than formaldehyde. The monomer was found to be only slightly active by comparison.

Gorman et al., *J. Clin. Pharm. Ther.* 12:393–399 (1987) reported on the examination of three antimicrobial agents, taurolidine, chlorhexidine, and povidone-iodine for microbial anti-adherence activity. Two adherence systems were investigated: an oral isolate of *Candida albicans* to human buccal epithelial cells and a urine isolate of *E. coli* to human uroepithelial cells. Each of the three agents exhibited significant anti-adherence activity, which was concentration dependent.

Root et al., *Antimicrobial Agents and Chemotherapy* 32(11):1627–1631 (1988) reported that granulocytopenic patients with an intravascular catheter are at increased risk for infection with *S. epidermis*. During the intervals when the catheters are not being used for infusions, it is customary to maintain patency of the catheter lumen with a solution containing heparin. The authors showed that heparin does not inhibit the growth of *S. epidermis* isolated from the catheter of an infected patient. A 20-mg/mL solution of disodium EDTA, a chelating agent that effectively anticoagulates blood at this concentration, was shown to be bactericidal for an initial inoculum of $10^3$ CFU of staphylococci per mL in 24 hours. Vancomycin, an antibiotic that is often employed to treat Staphylococcus infections was also found to be bactericidal for initial inocula of $10^3$ CFU/mL at doses of 6.7 $\mu$g/mL, a drug concentration in the therapeutic range. The authors recommended that EDTA be studied as a replacement for heparin solutions for the maintenance of intravenous catheters in granulocytopenic patients, in view of its low cost, effectiveness as an anticoagulant, and bactericidal activity.

Jones et al., J. Appi. Bacteriol 71:218–227 (1991) examined the effects of three non-antibiotic, antimicrobial agents—taurolidine, chlorhexidine acetate, and povidone-iodine—on the surface hydrophobicity of the clinical strains *E. coli, S. saprophyticus, S. epidermidis,* and *C. albicans*. At concentrations reported to interfere with microbial-epithelial cell adherence, all three agents were found to alter the cell surface hydrophobicity. However, these effects failed to exhibit a uniform relationship. Generally, taurolidine and povidone-iodine treatments decreased the hydrophobicity of the strains examined, whereas chlorhexidine acetate effects depended upon the micro-organism treated.

Traub et al., *Chemotherapy* 39:322–330 (1993) examined taurolidine for bactericidal activity against a representative number of multiple-antibiotic-resistant bacterial isolates in broth as well as in the presence of bovine and human serum and fresh defibrinated human blood. The authors suggested that this antimicrobial substance might be employed for topical treatment of patients colonized or superficially infected by glycopeptide-resistant strains of *E. faecium, S. aureus* (GRMRSA), or by Enterobacteriaceae producing wide-spectrum β-lactamases.

Willatts et al., *Crit. Care Med.* 23(6): 1033–1039 (1995) reported that taurolidine had no beneficial therapeutic effect on the outcome of patients admitted to the intensive therapy unit of a university teaching hospital with sepsis syndrome, using clinical, bacteriologic outcomes, progression of endotoxemia, resolution of organ failure, and 28-day mortality rate as end points.

Darouiche et al., *Nutrition* 13(4)(*suppl*):26S–29S (1997) reported that the prevention of vascular catheter-related infection mostly centers around inhibiting the adherence to the catheter of microorganisms originating from either the skin or the catheter hub. They described two general approaches that can be used non-exclusively for the successful prevention of vascular catheter-related infection. The first approach does not use antimicrobial agents and includes measures such as placement and maintenance of vascular catheters by a skilled infusion therapy team and use of maximal sterile barriers. The second approach uses antimicrobial agents and involves the application of topical disinfectants such as chlorhexidine, use of silver-impregnated subcutaneous cuffs (for short-term central venous catheters), flushing catheters with a combination of antimicrobial and antithrombic agents, and coating of catheters with either antiseptic (chlorhexidine and silver sulfadiazine) or antimicrobial agents (minocycline and rifampin).

In a talk presented at the 30th annual meeting of the American Society of Nephrology, held Nov. 2–5, 1997 in San Antonio, Tex., Sodemann et al. reported on a four year trial of a gentamicin/sodium citrate mixture as an antibiotic-lock technique for salvage and prevention of catheter-related infections. They concluded that the replacement of catheters due to infection can be avoided by routine application of the concentrated gentamicin/citrate mixture and that even the salvage of intraluminally contaminated catheters is possible.

Notwithstanding the above-described contributions to the art, a need continues to exist for a safe and effective method for the prevention of infection and blood coagulation in patients whose illness requires the implantation of atrial catheters.

SUMMARY OF THE INVENTION

In accordance with the present invention, compositions are provided that comprise an anticoagulant and a non-antibiotic biocide, neither of which have the properties of (a) inducing bacterial resistance and (b) causing systemic effects in the event of accidental overdose, i.e., there are no systemic anti-clotting and no systemic biocidal effects.

As employed herein, the term "anticoagulant" is intended to mean any composition that has the ability, either directly or indirectly, to prevent the coagulation of blood or to dissolve blood clots or other coagulated species once formed.

The biocide employed in the practice of the present invention is one that is a "non-antibiotic," i.e., it is not an antibiotic. For purposes of the present invention, the term "antibiotic" is defined as a chemical substance produced by a microorganism that has the capacity, in dilute solutions, to inhibit the growth of or to kill other microorganisms. It is an object of the present invention to avoid these antibiotics—although they may, if desired, be present in addition to the non-antibiotics of the invention—in order to minimize the probability of producing microorganisms that are genetically immune thereto. antimicrobial/anti-coagulant compositions are provided for use in flushing and coating medical prosthetic devices, especially catheters and ports.

Specifically, the present invention relates to a method of inhibiting or preventing infection and blood coagulation in or near a medical prosthetic device after said device has been inserted in a patient comprising administering to the device a pharmaceutically effective amount of a composition comprising:

(A) at least one taurinamide derivative, and
(B) at least one compound selected from the group consisting of biologically acceptable acids and biologically acceptable salts thereof, whereby there are no systemic anti-clotting and no systemic biocidal effects.

More particularly, the present invention is directed to a method of inhibiting or preventing infection and blood coagulation in or near a medical prosthetic device after said device has been inserted in a patient comprising administering to the device a pharmaceutically effective amount of a composition comprising:

(A) at least one antimicrobial compound of the formula

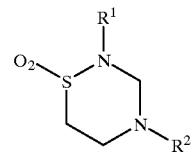

wherein $R^1$ is hydrogen or alkyl and $R^2$ is hydrogen, alkyl, or a group of the formula

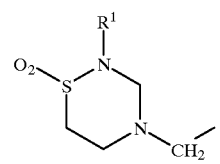

and (B) at least one compound selected from the group consisting of biologically acceptable acids and biologically acceptable salts thereof.

In another embodiment, the present invention is directed to a medical prosthetic device coated with a composition comprising:

(A) at least one antimicrobial compound of the formula

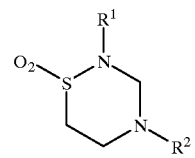

wherein $R^1$ is hydrogen or alkyl and $R^2$ is hydrogen, alkyl, or a group of the formula

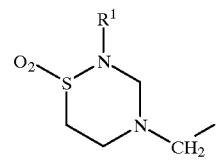

and (B) at least one compound selected from the group consisting of biologically acceptable acids and biologically acceptable salts thereof, wherein the composition is included in a pharmaceutically effective amount for preventing or inhibiting infection and blood coagulation.

In still another embodiment, the present invention is directed to a medical prosthetic device prepared by a process comprising exposing the medical prosthetic device to a composition comprising:

(A) at least one antimicrobial compound of the formula

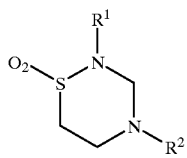

wherein $R^1$ is hydrogen or alkyl and $R^2$ is hydrogen, alkyl, or a group of the formula

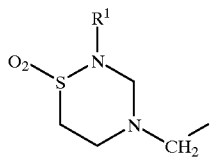

and (B) at least one compound selected from the group consisting of biologically acceptable acids and biologically acceptable salts thereof, wherein the composition is included in a pharmaceutically effective amount for preventing or inhibiting infection and blood coagulation.

DESCRIPTION OF THE PREFERRED EMBODIMENTS

As stated above, the present invention is directed to a method of inhibiting or preventing infection and blood coagulation in or near a medical prosthetic device after said device has been inserted in a patient comprising administering to the device a pharmaceutically effective amount of a composition comprising:

(A) at least one antimicrobial compound of the formula

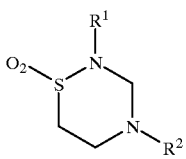

I wherein $R^1$ is hydrogen or alkyl and $R^2$ is hydrogen, alkyl, or a group of the formula

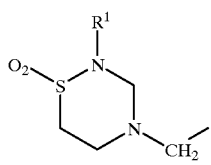

and (B) at least one compound selected from the group consisting of biologically acceptable acids and biologically acceptable salts thereof.

The preparation of representative examples of the compounds of formula I is described in U.K. Patent No. 1,124,285. Basically, these compounds are condensation products of taurinamide and formaldehyde and, therefore, will be referred to herein as "taurinamide derivatives." They are active not only against both gram-positive and gram-negative bacteria, but also against exotoxins and endotoxins produced by these organisms.

Where $R^1$ and/or $R^2$ are alkyl, they may be either straight or branched chain alkyl and are preferably independently selected from those alkyls having from 1 to 8 carbon atoms, i.e., methyl, ethyl, propyl, butyl, pentyl, hexyl, heptyl, octyl, and isomers thereof More preferably, where $R^1$ and/or $R^2$ are alkyl, they are independently selected from those alkyls having from 1 to 6 carbon atoms, i.e., methyl, ethyl, propyl, butyl, pentyl, hexyl, and isomers thereof, most preferably, the alkyl group(s) have from 1 to 4 carbon atoms, i.e., methyl, ethyl, propyl, butyl, and isomers thereof. It is, however, most preferred that $R^1$ be hydrogen and that $R^2$ be hydrogen or a group of formula II.

In the present invention, of the compounds of formula I, the compounds taurolidine ($R^1$=H; $R^2$=formula II) and taurultam ($R^1$=$R^2$=H) are particularly preferred. Taurolidine is bis-(1,1-dioxo-perhydroxy-1,2,4-thiadiazin-4-yl)methane.

The antimicrobial compound employed in the practice of the present invention is a formaldehyde carrier, i.e., a non-toxic derivative containing formaldehyde in combination.

The mode of action of taurolidine has been shown to include the transfer of methylol groups to hydroxyl or amino groups present on the above toxins or on the mureine of the bacterial cell walls. In solution, taurolidine exists in equilibrium with taurultam and N-methylol taurultam, taurolidine being greatly predominant. Taurultam is itself in equilibrium with methylol taurinamide, the equilibrium being greatly in favor of taurultam. When the above methylol derivatives, methylol taurultam and methylol taurinamide, contact the toxins or bacteria, methylol groups are transferred. Methylol taurultam is thereby converted to taurultam, while methylol taurinamide is converted to taurine, a naturally occurring aminosulfonic acid that is extremely well tolerated in the human body. It will thus be appreciated that taurolidine and taurultam act in essentially the same way and produce the same final products.

Bacterial infections by gram-negative organisms are commonly accompanied by endotoxaemia, that is, by the reaction of the patient to the endotoxin liberated by the organisms.

Endotoxin is a complex lipopolysaccharide constituent of the O-somatic antigen and is loosely attached to the cell walls of gram-negative bacteria. Irrespective of the bacterial source, all endotoxins exhibit similar toxic properties—in contradistinction to the exotoxins of gram-positive bacteria, which exert a wide range of individual effects. In man, it can produce the syndrome of endotoxin shock when large numbers of gram-negative bacteria are lysed. This syndrome is encountered in about 30% of patients with gram-negative septicaemia. It is known that endotoxins can be inactivated by taurinamide derivatives.

Toxic proteins, such as, exotoxins, can similarly be inactivated and methylol transfer antibacterials can be administered to combat toxic proteins in the absence of lipopolysaccharide toxins. Toxins that may be concerned include the exotoxins of such gram-negative bacteria as *E. coli* and *Bacteroides fragilis*. It is known that intravenous administration to mice of 0.2 mL of a 20% solution of taurolidine in sterile 5% polyvinyl pyrrolidone can very significantly reduce the mortality rate on intraperitoneal administration of pathogenic strains of both *E. coli* and *B. fragilis*.

Other toxic proteins include venoms such as mellitin and fungal toxins such as amanitin and α-bungarotoxin, which have been shown to be substantially detoxified by taurolidine.

A particular advantage of taurolidine is its very low toxicity; it has been shown to be non-teratogenic in mice, the intraperitoneal $LD_{50}$ being on the order of 1.5 g/kg. As mentioned above, these compounds exhibit methylol transfer activity that results in the production of taurine, which is found naturally in the body and is particularly nontoxic. A further advantage of taurolidine is its stability in aqueous solution, enabling the solutions to be pre-packed and stored over relatively long periods.

The taurinamide derivatives employed in the practice of the present invention will normally be administered as an aqueous solution by injection into the medical prosthetic device. Such solutions may contain, in addition to a given taurinamide derivative, gentamycin sulfate or chondroitin sulfate and also may commonly contain a solubilizing agent, such as, polyvinyl pyrrolidone (PVP), to help maintain the taurinamide derivative in solution and to contribute to the isotonicity of the solution. The concentration of the taurinamide derivatives in such solutions can range from greater than zero to about 2 wt %, concentrations in the range of from about 0.01 to about 1.5 wt % are preferred; and a concentration of about 1 wt % is most preferred. Higher concentrations than these would be useful, but in such cases, solubility becomes a problem.

Where PVP is incorporated into the solution, it will commonly be employed at a concentration in the range of from 4 to 7% by weight in order to achieve relatively high concentrations of the taurinamide derivatives, especially taurolidine, which have low water solubility. The molecular weight of the PVP should not be greater that about 30,000 and is preferably less than 10,000, e.g., between about 200 and 3500. Kollidone® 17, sold by BASF is especially suitable. Such PVP is fairly quickly absorbed and excreted through the kidneys.

The amount of solution of taurinamide derivative injected into a medical prosthetic device will be enough to fill it. Such devices, when they are hemodialysis catheters, typically have internal volumes in the range of from about 0.1 mL to about 10 mL; such quantities will, of course, vary with the length and diameter of the tubing of the device, which, inter alia, can be a function of the size of the individual patient.

The concentration of the taurinamide derivative in such solutions is preferably in the range of from about 0.4 to about 5% by weight, depending, at the maximum, upon the solubility of the compound. Solutions of about 0.4 to about 2.0 weight % taurolidine, i.e., about 4 to about 20 grams per liter, are particularly preferred.

An example describing the preparation of a stock solution of taurolidine has appeared in several patents, for example, U.S. Pat. No. 4,337,251:

15 Liters of double distilled pyrogen free water are filled into a 25 liter glass vessel equipped with a stirrer and an intensive reflux device and heated to 50° C. with stirring. Taurolidine (400 g) is added followed by PVP (Kollidone 17; 1000 g). After dissolution, the solution is cooled and the pH is adjusted to 6.0 with a few drops of 0.1 N hydrochloric acid. The solution is then passed through an adsorption filter to remove microorganisms and pyrogens and through a sterilizing Millipore filter before being filled into 100 mL vials, which are finally autoclaved.

If desired, some or all of the PVP may be replaced by a parenterally acceptable polyol. This use for polyols has been disclosed in U.S. Pat. No. 5,210,083, the disclosure of which is incorporated herein by reference in its entirety. There, it is pointed out that at higher concentrations of taurolidine, crystallization can occur, which can render the solution unuseable.

In the case of bacteria and their endo- and exotoxins, it has been found that after the methylol transfer, as described above, there is a further irreversible step involving dehydration. Thus, in the case of bacterial endotoxins, which are lipopolysaccharides, it was found that an irreversible cross-linking reaction takes place that prevents the endotoxin from exerting its lethal effect. Similarly, in the case of bacterial exotoxins, which are proteins or polypeptides and do not contain lipopolysaccharide material of the kind found in the endotoxins, the detoxification reaction has been found to be irreversible. However, it is disclosed in U.S. Pat. No. 5,210,083 that the transfer of methylol groups by the mechanism set out above is reversible in the case of many hydroxyl or amino compounds, so that an equilibrium can be established that does not significantly interfere with the availability of taurolidine. Thus, polyols, such as, sugars and sugar alcohols, can also be used to maintain relatively high concentrations of taurolidine and/or taurultam in aqueous solution without significantly affecting their antibacterial and antitoxin activity Preferred polyols include carbohydrates, e.g., hexoses, such as, glucose, fructose, and mixtures thereof; pentoses, such as, xylose; polysaccharides, such as, dextran or hydrolyzed starch; glycerol; and sugar alcohols, such as, sorbitol, mannitol, and xylitol. Glucose is most preferred.

The concentration of the polyol is typically in the range of from about 3 to about 40% by weight. In the case of glucose, the concentration is preferably in the range of from about 10 to about 30% by weight, more preferably about 20%.

Where such polyols are used, the concentration of taurolidine in the solution is preferably in the range of from about 0.5 to about 5%, more preferably in the range of from about 2 to about 3% by weight. The concentration of taurultam is preferably in the range of from about 1 to about 7.5%, more preferably in the range of from about 3 to about 5% by weight.

However, recent experiments have shown that neither PVP nor polyols are neccessary for increasing the solubility of taurolidine in aqueous solutions. In fact, these experiments have shown that addition of citrric acid substantially increases solubility of taruolidine in water and that PVP is not really effective in increasing the solubility. In these experiments, researchers prepared a series of solutions using approximately 2.6% by weight of citric acid to aid solubility and achieved solutions with 1.0, 2.0, 3.0 4.0 weight percent of taurolidine in solution with no PVP or poylol. Reseachers beliece that additonal citric acid will easily raise the taurolidine solubility to 5% without polyol or PVP. In fact, these researchers found substantially no effect on solubility of added PVP. The foregoing experiemental solutions were brought into a pH range acceptable for biological application by adjustment with sodium hydroxide to the range of pH 5.2 to 5.3. This approach creates a buffer system of citric acid/sodium citrate.

In addition, citric acid is a known antioxidant. The buffer system created by adjustment of pH using sodium hydroxide also resists changes in the pH due to the oxidation of formaldehyde to formic acid. Thus the use of citric acid and sodium citrate in this combination increases the stability of taurolidine in solution and prevents or severely slows down the precipitation out of solid taurolidine and reaction products frequently seen in taurolidine solution prepared with PVP. Long term stability tests have verified this result.

Since gram-negative organisms will frequently be present and since the bacteriostatic activity of the taurinamide derivatives is lower than that of many conventional antibiotics, it may be advantageous to administer the compositions employed in the practice of the present invention in conjunction with a broad spectrum antibiotic substance, more especially, a substance strongly active against both gram-positive and gram-negative pathogens that, preferably, induces no or only delayed resistance, for example, a β-lactam antibiotic, such as, penicillin, ampicillin, or cephalosporin; a tetracycline antibiotic; a macrolide antibiotic, such as, erythromycin; a polypeptide antibiotic, such as, bacitracin or novobiocin; or, more preferably, an aminoglycoside antibiotic, such as, amikasin, butirosin, fortimycin, streptomycins, neomycin, linkomycins, such as, clindamycin and lincomycin, kanamycin, dideoxykanamycin B (DKP), lividomycin, netilmicin, ribostamycin, sagamycins, seldomycins and their epimers, sisomycin, sorbistin, tobramycin, vancomycin, gentamicin, and rifamycins, such as, rifampicin and rifamycin; and the like. Of these, gentamicin is preferred.

However, antibiotics are often contraindicated for use in surgical treatment, owing to their tendency to produce resistant strains, and, except in unusual cases, it is preferred that the taurinamide derivative be relied upon solely for antibacterial action, since such derivatives do not produce resistant strains.

The composition employed in the practice of the present invention preferably also contains a pharmacologically acceptable carrier solution, such as, water, Ringer's solution, or saline. Additionally, the compositions of the present invention can also contain other dissolved additives that can favorably influence their physical and biochemical properties, for example, amino acids, sugar, common salt, fats, lipids, and the like.

The antimicrobial taurinamide derivatives employed in the practice of the present invention are used in combination with a biological acceptable acid or a biologically acceptable salt thereof. It is preferred that the acid be a carboxylic acid and more preferred that it be an anticoagulant. U.S. Pat. No. 5,077,281 teaches that taurolin compounds exhibit outstanding coagulation-inhibiting action in their own right and are especially suitable for use in medical conditions requiring dialysis and for vascular prostheses, either alone or in combination with other anti-coagulants such as coumarin or heparin. As pointed out in the patent, this is contrary to the teaching of "Taurolin", published by W. L. Bruckner and R. W. Pfirrmann, Verlag Urban und Schwarzenberg, Munich, 1985, which expressly states that taurolin does not influence blood coagulation and displays no anti-phlogistic action. It is the belief of the present inventor that the taurinamide derivatives employed in the practice of the present invention do exhibit a degree of anticoagulant activity, although to a lesser extent than is found with better known anticoagulants, such as heparin. Accordingly, it is beneficial to employ the taurinamide derivatives in combination with an anticoagulant, preferably one that is a biologically acceptable acid or salt thereof.

In accordance with the present invention, beneficial results are achieved when the antimicrobial taurinamide derivatives are combined with a biologically acceptable acid or biologically acceptable salt thereof so as to produce a pH for the ultimate composition that is no higher than 7, preferably in the range of from about 3.5 to about 6.5, more preferably in the range of from about 4.5 to about 6.5. Exemplary of such acids are acetic acid, dihydroacetic acid, benzoic acid, citric acid, sorbic acid, propionic acid, oxalic acid, fumaric acid, maleic acid, hydrochloric acid, malic acid, phosphoric acid, sulfurous acid, vanillic acid, tartaric acid, ascorbic acid, boric acid, lactic acid, ethylenediaminetetraacetic acid (EDTA), ethylene glycol-bis-{β-aminoethyl ether}-N,N,N',N'-tetraacetic acid, and diethylenetriamine pentaacetic acid, esters of p-hydroxybenzoic acid (Parabens), and the like, and biologically acceptable salts of the foregoing, such as, ammonium phosphate, potassium citrate, potassium metaphosphate, sodium acetate, sodium citrate, sodium lactate, sodium phosphate, and the like. A blood anticoagulating amount of an acid selected from the group consisting of citric acid, phosphoric acid, ethylenediaminetetraacetic acid (EDTA), ethylene glycol-bis-{β-aminoethyl ether}-N,N,N',N'-tetraacetic acid, and diethylenetriamine pentaacetic acid and biologically acceptable salts thereof is preferred. It is preferred that the acid employed in the practice of the present invention be an organic acid, especially one having at least one carboxyl group, particularly citric acid or EDTA. It is more preferred that the acid be citric acid and most preferred that it be used in combination with a citrate salt, e.g., sodium citrate, since, in addition to its pH lowering and anticoagulation capabilities, it is also known to be an antiseptic at the 3% level.

Mermel, L. A. et al., in a talk entitled *Taurolidine Activity Against Vancomycin-Intermediate Susceptibility Staphylococcus Aureus (VISA) and Methicillin-Resistant Staphylococcus Aureus (MRSA)* presented at the Interscience Conference on Antimicrobial Agents and Chemotherapy (1998), disclosed that taurolidine activity increases with decreasing pH in the range of from pH 7.0 to pH 5.0.

EDTA is a known anticoagulant that is used in blood collection tubes. It is also known to have the ability to form chelates with calcium. Since calcium is one factor that is known to have a role in the coagulation of blood, it is believed possible that at least part of EDTA's efficacy in anticoagulant activity may be brought about by this means. Sodium citrate is also believed to have anticoagulation properties by virtue of its ability to generate insoluble calcium citrate.

Ethylene glycol-bis-{β-aminoethyl ether}-N,N,N',N'-tetraacetic acid (EGTA) and diethylenetriamine pentaacetic acid (DTPA) and salts thereof are other known chelating agents that can be used in place of, or in addition to, EDTA or citric acid/citrate.

The foregoing anticoagulants can be used alone in the free acid state, but, more often will be employed with some or all of their carboxylic acid groups neutralized with an appropriate base or combined with a similar salt. Generally, it will be desirable to employ a cation that will form a salt that is soluble in aqueous solution, such as alkali metal ions, e.g., sodium, potassium, or lithium. Zinc citrate may also be employed. Sodium or potassium salts are normally preferred, especially sodium, and the disodium salt of EDTA and sodium citrate and most preferred.

The acid and/or salt will be used in a concentration effective to bring about the desired anticoagulation effect and, at the same time, bring about, or help to bring about, an appropriate pH for biological use. Typically, the combined antimicrobial and anticoagulant composition of the present invention will have a pH in the range of from about 3.0 to about 7, preferably from about 3.5 to about 6.5 and, most preferably from about 4.5 to about 6.5. The composition will normally be at a physiological pH. If necessary, the pH can be adjusted by additional acid or base, such as a mineral acid, for example hydrochloric acid, or, preferably, one that will not cause acidosis, such as, for example, acetic, malic, or lactic acid. Other methods for adjusting the pH, familiar to those of skill in the art, can also be employed. Where, as is preferred, trisodium citrate and citric acid are employed in the practice of the present invention, the trisodium citrate will typically be used in a concentration range of from about 5 to about 50 grams per liter. The citric acid will then be added in sufficient amount to bring the pH to the desired level.

Although the process of the present invention is primarily concerned with introducing the antimicrobial/anticoagulant compositions into catheters that are already in place, those skilled in the art will understand that contacting an artificial surface outside the body with these compositions can prevent the deposition of blood coagula on such surface after its implantation and aid in the elimination of sites for bacterial growth. Thus, the surfaces of medical devices, such as hemodialysis catheters, can be pre-treated by the compositions employed in the practice of the present invention to prevent the blockage due to blood coagula that present a favorable site for bacteria growth and thereby prevent the infection that may ensue. The apparatus can be treated with a composition initially and then, after insertion, repeated periodic flushing as referred to above.

Although the process of the present invention is primarily and preferably directed to maintaining the patency and asepsis of implanted hemodialysis catheters, beneficial effects may also be obtained in applying the process to other, similar, devices, such as, central venous catheters, peripheral intervenous catheters, arterial catheters, Swan-Ganz catheters, umbilical catheters, percutaneous nontunneled silicone catheters, cuffed tunneled central venous catheters as well as with subcutaneous central venous ports.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLE 1

A 0.5% solution of taurolidine in Ringer-lactate solution (Thomae, Biberach, Germany) was introduced into each of four polyethylene bottles having a 30 mL volume. Filling volumes were 5, 10, and 15 mL. One bottle was filled with 5 mL of the taurolidine solution and 2 mL ACD-A (Fresenius, Bad Homburg, Germany) solution. ACD-A solution is used for the conservation of whole blood and contains per liter: 22.0 grams of sodium citrate dihydrate, 7.3 grams of citric acid and 34.5 grams of glucose monohydrate.

Blood was collected at the slaughter house from a female pig directly from the slaughter wound into the containers that were then filled up to the 30 mL level. The containers were capped and gently moved to mix blood with the solution. The containers were inspected after 30 minutes. Blood in the containers containing only taurolidine was clotted, but the blood in the container containing the mixture of taurolidine and ACD-A was not clotted. Thus, it is concluded that the use of sodium citrate and citric acid anticoagulants in combination with taurolidine provides substantially enhanced anticoagulation properties in whole blood.

EXAMPLE 2

A subcutaneously implantable titanium port-system of the type described in U.S. patent application Ser. No. 08/485,498 is used in this example. It is connected with two 12 French silastic catheters introduced with the tips into the right atrium. The valves of the port are opened by two special needles allowing a blood flow of about 300 mL/min.

Ports were implanted by an experienced nephrologist, after their informed consent, in 10 female and 6 male patients, whose mean age was 68±9 years. Nine of the sixteen patients were diabetics. Patient inclusion criterion for the study was vessel exhaustion resulting in no blood access sites in the arms available for hemodialysis. Eight of the sixteen suffered from severe congestive heart failure and all had a high comorbidity. Nine of the patients started hemodialysis just after implantation, the others were on chronic hemodialysis and switched from catheter to the port system (four patient exchange by guidewire). No perioperative complications occurred.

The preferred vessel was the right internal jugular vein, but the external jugular and subclavian veins were also used. The device has, thus far, been used for a total duration of 11.0 patient years. The ports were used for all planned IID sessions (n=1200).

In order to avoid intraluminal contamination of the device, an antimicrobial lock was applied between the sessions and removed before the next treatment. The aqueous antimicrobial lock solution comprised 13.3 grams/liter of taurolidine, 6.7 grams per liter of tri-sodium citrate, and approximately 3.3 grams per liter of citric acid. The citric acid was added to adjust the pH range to 4.75–5.25. By virtue of the citric acid and sodium citrate, clotting of the catheters was prevented and application of heparin was unnecessary.

During the period of the study, two episodes of bacteriaemia (*S. aureous*) were observed and successfully treated without loss of the device (0.5 infection per 1000 days). The results of this study are shown in Table 1.

EXAMPLE 3

Comparative Example

In four separate facilities, two in the United States and two in Europe, A, B, C, and D, studies similar to those described above in Example 2 were carried out, except that the lock used was heparin or heparinized saline in concentrations in the range of from 2,000 to 10,000 international units per mL. In the studies in the United States, A and B, benzyl alcohol was also present as a standard presevative. The results of these comparative studies are shown in Table 1.

TABLE 1

| | | | | Infections | | | Fibrin/Thrombosis | |
| --- | --- | --- | --- | --- | --- | --- | --- | --- |
| Example | No of Patients | Time Pat. Yrs. | Explant for Cause (#s) | Number | Patients Affected (%) | Mean Interval[1] (Weeks) | Number | Mean Interval[2] (Weeks) |
| 2 | 31 | 11.0 | 0 | 2 | 7 | 286 | 0 | >500 |
| 3A | 8 | 8.0 | 1 | 6 | 50 | 70 | 2 | 208 |

TABLE 1-continued

| Example | No of Patients | Time Pat. Yrs. | Explant for Cause (#s) | Infections | | | Fibrin/Thrombosis | |
|---|---|---|---|---|---|---|---|---|
| | | | | Number | Patients Affected (%) | Mean Interval[1] (Weeks) | Number | Mean Interval[2] (Weeks) |
| 3B | 4 | 4.2 | 2 | 10 | 75 | 22 | 4 | 54 |
| 3C | 7 | 6.1 | 2 | 6 | 43 | 53 | 4 | 79 |
| 3D | 4 | 3.4 | 0 | 0 | 0 | >176 | 0 | >176 |
| Total (Ex. 3) | 23 | 21.7 | 4 | 22 | 44 | 51 | 10 | 113 |

[1]Mean interval without infection.
[2]Mean interval without clotting.

EXAMPLE 4

In this example, which is a more detailed description of the trial of Example 2, the subcutaneously implantable titanium port-system described in Example 2 was used.

In a prospective multi-center pilot trial starting June, 1998, 31 ports were implanted in 19 female and 12 male patients (mean age 66, min. 30, max. 81 years). In addition to the acceptance of the new device, the aim of the study was the avoidance of infection supported by the completely atoxic mixture (heparin-free lock solution containing taurolidine as an anti-infective substance and citric acid/sodium citrate for inhibition of coagulation) with excellent efficacy against any germs, even those with multi-resistance.

In ten participating centers, no port was lost since the start of the study (3,847 days of implantation). Despite high comorbidity, only two patients experienced blood-stream related infections (S. aureus). Total observed infection was 0.5 per 1000 days. Systemic antibiotic treatment was successful. Pre-existing catheter-related sepsis occurred in 5/31 patients; no relapse occurred in the patients using the subcutaneously implantable titanium port-system.

Hospitalization was short and access was used just after implantation. The acceptance was high even in patients who switched from catheter to port (12/3 1). In 6/31 patients an exchange by guide-wire was possible. The usual placement technique was Seldinger applied by three nephrologists. The preferred vessel was the right internal jugular vein (18/31), but all other central veins were used.

Compared to the disadvantages of catheters, the port system allows bathing and is very safe. Combined with the lock solution of the present invention, the risk of infection is low and allows a puncture technique similar to a graft. The lifetime of the device has yet to be established.

EXAMPLE 5

An experiment was conducted to determine the minimum taurolidine/citrate lock solution acidity that will function well when in contact with human blood. Various lock solution acid concentrations were mixed 50/50 by weight with fresh whole human blood. The pH was experimentally varied from pH 3.0 to pH 7.0. At a lock solution acidity level of 4.0 and below, the resulting blood mixture becomes hard and concretionary after one hour of contact with the lock solution. This hardening was apparently due to the acid level of the lock solution and normal blood clotting, since the clot appears very dark in color and dry in nature, not normal in color or physical properties. When acidity of the lock solution was maintained above pH 5.0, no blood clotting occurred and blood color remained a healthy red color. Thus, the most preferred lower limit for the acidity of the taurolidine lock solution is about 5.0.

In view of the many changes and modifications that can be made without departing from principles underlying the invention, reference should be made to the appended claims for an understanding of the scope of the protection afforded the invention.

What is claimed is:

1. A composition comprising (A) at least one antimicrobial compound of the formula

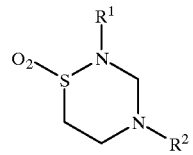

(B) citric acid in an amount sufficient to raise the solubility of said at least one antimicrobial compound to the range of 2 to 5%; and (C) sodium hydroxide in sufficient quantity to raise the pH of the solution to at least the range of 5.2 to 5.3, whereby a buffer system of citric acid and sodium citrate develops.

2. The composition of claim 1 in which the at least one antimicrobial substance is taurolidine.

3. A method of increasing the solubility of taurolidine in aqueous solutions by adding citric acid.

4. The method of claim 3 additionally comprising the step of adding sodium hydroxide to adjust the pH of the solution and create a buffer system of citric acid and sodium citrate.

* * * * *